United States Patent [19]

Müeller et al.

[11] Patent Number: 4,661,610

[45] Date of Patent: Apr. 28, 1987

[54] PREPARATION OF VERATRYL CYANIDE

[75] Inventors: Josef Müeller, Grosskarlbach; Walter-Wielant Wiersdorff, Mutterstadt; Wolfram Bürst, Mannheim; Heinz Dralle, Minden; Ernst Schäffner, Minden; Rolf Steinkamp, Minden, all of Fed. Rep. of Germany

[73] Assignee: BASF Aktiengesellschaft, Fed. Rep. of Germany

[21] Appl. No.: 887,940

[22] Filed: Jul. 22, 1986

[30] Foreign Application Priority Data

Jul. 31, 1985 [DE] Fed. Rep. of Germany ....... 3527338

[51] Int. Cl.$^4$ ............................................ C07C 120/04
[52] U.S. Cl. ......................................................... 558/344
[58] Field of Search ............................................ 558/344

[56] References Cited

U.S. PATENT DOCUMENTS 2,734,908  2/1956  Dengel ................................ 260/465

FOREIGN PATENT DOCUMENTS 9451  3/1955  Fed. Rep. of Germany .
3341306  5/1985  Fed. Rep. of Germany .

OTHER PUBLICATIONS

Knabe et al., J. Knabe, Arch. Pharmaz. 296, 591 (1963).
Fujii et al., J. Knabe, Arch. Pharmaz. Bull, 19, 1374 (1971).
Stroh et al., "Herstellung von Chlorverbindungen", Houben Weyl, Methoden der org. Ch., 4th ed., Georg-Thieme Publisher, Stuttgart 1962, vol. 513, p. 1001.

Primary Examiner—Dolph H. Torrence
Attorney, Agent, or Firm—Keil & Weinkauf

[57] ABSTRACT

Veratryl cyanide is prepared by chloromethylating veratrol in solution in toluene and then reacting the resulting veratryl chloride with from 1 to 5 moles of an alkali metal cyanide, by a process in which the toluene from the chloromethylation is not removed for the reaction with cyanide, and from 3 to 25% by weight, based on veratryl chloride, of water, from 5 to 50% by weight, based on toluene, of a ketone of 3 to 6 carbon atoms and from 0.1 to 10% by weight, based on veratryl chloride, of a phase transfer catalyst are added before the reaction with cyanide.

1 Claim, No Drawings

PREPARATION OF VERATRYL CYANIDE

The present invention relates to a process for the preparation of veratryl cyanide (VCN), wherein the toluene solution of the veratryl chloride obtained by chloromethylation of veratrol is reacted directly with sodium cyanide, with the addition of water, a ketone and a catalyst.

Veratryl cyanide is an important intermediate in the pharmaceutical industry and is used, for example, for the preparation of verapamil and papaverin.

Since, on the one hand, the chloromethylation of alkoxybenzenes, such as veratrol, is carried out in toluene as the solvent, and, on the other hand, further processing of the resulting veratryl chloride to veratryl cyanide is effected in a polar solvent, the solvent has to be changed in the conventional processes (U.S. Pat. No. 2,734,908, Arch. Pharm. 296, (1963) 591). Apart from the fact that the method is technically complicated and energyconsuming, the removal of the toluene by distillation results in a considerable loss of yield, owing to the thermal instability of the veratryl chloride.

U.S. Pat. No. 2,734,908 describes the reaction of veratryl chloride with a cyanide in a ketone, with the addition of an alkali metal iodide. However, this procedure is disadvantageous since the very long reaction times and low concentrations result in low space-time yields. To work up the mixture, it has to be filtered off from the salt residue, the solvent has to be distilled off and the residue has to be dissolved in a second solvent. The mixture is then subjected to fractional distillation. These operations are technically complicated and expensive.

Arch. Pharm. 296 (1963) 591 describes the same reaction in dimethylformamide, with the addition of 5% of $H_2O$, the yield obtained being 85%. In this case too, the problem of separating off the salt arises. Chem. Pharm. Bull 19 (1971) 1374 refers to the formation of by-products in this process.

German Patent application No. P 33 41 306.1 describes the reaction of p-methoxybenzyl chloride with cyanide in methyl isobutyl ketone with the aid of a phase transfer catalyst and with the addition of water. Although good yields and space-time yields are obtained here, the process is likewise unsuitable for the industrial synthesis of VCN, since the chloromethylation of veratrol cannot be carried out successfully in methyl isobutyl ketone and, if the conventional solvent, toluene, has been used for the prior chloromethylation of veratrol, a change of solvent would be necessary, resulting in substantial decomposition of the thermally unstable veratryl chloride.

It is an object of the present invention to provide an industrial process for the preparation of veratryl cyanide, the process being simpler than the conventional processes and constitutes an improvement from the technical and economic points of view.

We have found that this object is achieved by a process for the preparation of veratryl cyanide by chloromethylating veratrol in solution in toluene and then reacting the resulting veratryl chloride with from 1 to 5 moles of an alkali metal cyanide, wherein the toluene from the chloromethylation is not removed for the reaction with cyanide, and from 3 to 25% by weight, based on veratryl chloride, of water, from 5 to 50% by weight, based on toluene, of a ketone of 3 to 6 carbon atoms and from 0.1 to 10% by weight, based on veratryl chloride, of a phase transfer catalyst are added before the reaction with cyanide.

The synthesis takes place according to the following equation:

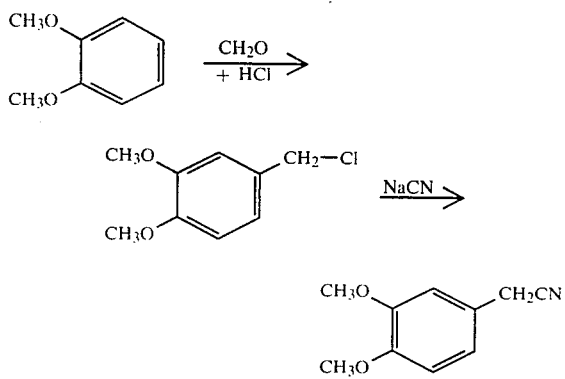

The chloromethylation of the veratrol in toluene is carried out by conventional methods, as described in, for example, East German Patent No. 9,451 and Houben-Weyl, Methoden der organischen Chemie, 4th edition, Georg-Thieme Verlag, Stuttgart 1962, vol. 5/3, page 1001.

The reaction of the veratryl chloride with cyanide may be carried out as follows: a mixture of toluene, a ketone, veratryl chloride, an alkali metal cyanide, a phase transfer catalyst and water in the proportions stated in the claim is kept at from 50° to 95° C. for from 1 to 5 hours. Compared with the conventional processes, the process according to the invention gives veratryl cyanide in better yield, space-time yield and purity. The isolation of the end product from the salts does not require any additional solvent. The content of the undesirable by-product veratryl alcohol is low; this makes working up, in particular the fractional distillation of the veratryl cyanide, simple to carry out.

Another important advantage of the novel process is that the solution of crude veratryl chloride in toluene, obtained from the chloromethylation, can be used directly, i.e. without a change of solvent, in the cyanization stage. This is carried out with the addition of small amounts of a ketone (from 5 to 50, preferably from 7 to 15, % by weight, based on toluene), of a phase transfer catalyst (from 1 to 10, preferably from 1 to 3, % by weight, based on veratryl chloride), and of water (from 3 to 25, preferably from 5 to 10, % by weight, based on veratryl chloride).

The alkali metal cyanide is used in an amount of from 100 to 500, preferably from 110 to 150, mol %, based on veratryl chloride. Preferred alkali metal cyanides are potassium cyanide and in particular sodium cyanide.

The ketones used are those of the formula

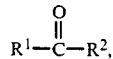

where $R^1$ is methyl or ethyl and $R^2$ is alkyl of 1 to 4 carbon atoms, with the proviso that the total number of carbon atoms in $R^1$ and $R^2$ is from 2 to 5, or where $R^1$ and $R^2$ together with the carbonyl group may furthermore form a 5-membered or 6-membered ring.

Examples of suitable ketones are methyl ethyl ketone, diethyl ketone, methyl propyl ketone, methyl isobutyl ketone, methyl n-butyl ketone, methyl sec.-butyl ketone, methyl tert.-butyl ketone, cyclopentanone and cyclohexanone, preferably methyl ethyl ketone, diethyl ketone and cyclopentanone, in particular acetone.

Phase transfer catalysts are catalysts which improve the transport of substances in binary liquid systems (consisting of water and an organic solvent). Even small amounts of catalyst produce the transfer effect, i.e. the starting materials pass from one phase into the other with the aid of a small amount of catalyst. Regarding the definition, preparation and properties of such phase transfer catalysts, reference may be made to, for example, J. Amer. Chem. Soc., 93 (1971), 195 and to Chem. Education, 55 (1978), 429, 350.

Advantageous phase transfer catalysts are quaternary salts, in particular catalysts of the formula

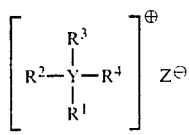

where the individual radicals $R^1$, $R^2$, $R^3$ and $R^4$ are identical or different and are each an aliphatic, cycloaliphatic, aromatic or araliphatic radical, Y is nitrogen or phosphorus and Z is an acid anion. Preferred catalysts are those of the formulae in which the individual radicals $R^1$, $R^2$, $R^3$ and $R^4$ are identical or different and are each alkyl or hydroxyalkyl, each of 1 to 18, in particular 1 to 7, carbon atoms, cycloalkyl of 5 to 8 carbon atoms, aralkyl or alkylaryl of 7 to 12 carbon atoms or phenyl. However, it is also possible to use tertiary amines in conjunction with an alkyl iodide. The system triethylamine/sodium iodide in a molar ratio of from 1:0.5 to 1:1.5 is particularly preferred.

Examples of suitable phase transfer catalysts are tetramethyl-, tetra-n-propyl-, tetraisopropyl-, tetra-n-butyl-, tetraisobutyl-, tetra-sec.-butyl-, tetra-tert.- butyl-, tetrapentyl-, tetrahexyl-, tetra-n-heptyl-, tetra.-octyl-, tetranonyl-, tetradecyl-, tetraethyl-, tetraundecyl and tetradodecylammonium chloride; tetra- -hydroxyethylammonium chloride, tetra-α-hydroxypropylammonium chloride, tetra-ω-hydroxypropylammonium chloride, tetra-γ-hydroxybutylammonium chloride, tetra-ω-hydroxybutylammonium chloride, tetra-β-hydroxybutylammonium chloride, tetra-(α, α-dimethyl-β-hydroxyethylammonium chloride, tetra-(α-methyl-β-hydroxypropyl)-ammonium chloride, tetra-( β, β-dimethyl-β-hydroxyethyl)-ammonium chloride, tetra-(α-ethyl-β-hydroxyethyl)-ammonium chloride, tetra-(α-methyl-ω-hydroxypropyl)-ammonium chloride, tetra-(β-methyl-ω-hydroxypropyl)-ammonium chloride, tetra-β-hydroxypentylammonium chloride, tetra-δ-hydroxypentylammonium chloride, tetra-γ-hydroxypentylammonium chloride, tetra-ω-hydroxypentylammonium chloride and tetra-β-hydroxypentylammonium chloride; corresponding ammonium chlorides obtained by quaternary substitution with abovementioned substituents and/or with phenyl, benzyl, cyclohexyl, toluyl, methylcyclohexyl, phenylethyl, phenylpropyl or phenylbutyl on the nitrogen atom from anilyl-amine, o-, m- or p-toluidine, triphenylamine, tribenzylamine, tricyclohexylamine, tri-(methylcyclohexyl)-amine, tri-(phenylethyl)-amine, tri-(phenylpropyl)-amine, tri-(phenyl-butyl)-amine, or triphenylamine which is monosubstituted in the 2-, 3- or 4-position or disubstituted in the 2,4-, 2,3-, 2,6-, 2,5-, 3,4- or 2,5-position by methyl on each phenyl ring, where the said ammonium chlorides may include those having 4 radicals among those mentioned above, some or all of which differ from one another, for example the quaternary ammonium chlorides obtained from N,N-dimethylaniline, N-methyl-N,N-diethylamine, N,N-dicyclohexyl-N-methylamine, or N-methyl-N-ethyl-N-n-propylamine by substitution with methyl, or, for example, dimethylbenzyldodecyl-, cetyltrimethyl-, methyltriethyl-, dimethyldiphenyl-, trimethyl-(o-tert.-butylphenyl)-, triethyldodecyl-, trimethyltridecyl-, trimethyldiphenylmethyl-, trimethyl-N-dodecyl-, trimethyl-β-hydroxyethyl-, N-propyltrimethyl-, isoamyl-trimethyl-, benzyldimethyl-n-octyl-, benzyltrimethyl-, benzyltriethyl-, phenyltrimethyl-, dimethyldodecylphenyl-, trimethylphenyleth-1-yl- or trimethylphenyleth-2-ylammonium chloride, and corresponding ammonium bromides; homologous quaternary ammonium salts of inorganic or organic monobasic or polybasic acids, such as hydrochloric acid, hydrobromic acid, hydroiodic acid, perchloric acid, sulfuric acid, phosphoric acid, nitrous acid, nitric acid or carbonic acid, sulfonic acids, such as benzenesulfonic acid or p-toluenesulfonic acid, boron-containing acids, such as boric acid or fluoboric acid, or mixtures of these. The quaternary ammonium salts of hydrochloric acid, hydrobromic acid, sulfuric acid or phosphoric acid, having the abovementioned substituents on the heteroatom and/or acid anions, and homologous phosphonium salts are preferred.

The amount of phase transfer catalyst which is used in the cyanization is from 0.1 to 10, preferably from 1 to 3, % by weight, based on veratryl chloride employed. The reaction can be carried out continuously or batchwise at from 50° to 95° C., but is particularly preferably effected at from 80° to 88° C. (under reflux).

The reaction time is from 1.0 to 5, preferably from 1.5 to 2.5, hours. This is substantially shorter than the time required in the conventional processes, where the total time for solvent change and reaction is from 10 to 40 hours. The end of the reaction can be detected by, for example, thin layer chromatography or gas chromatography.

The end product can be isolated from the reaction mixture in a conventional manner, for example by the addition of water, phase separation and distillation.

In the Examples which follow, parts are by weight.

EXAMPLE 1

87 parts of toluene, 2.4 parts of water, 18.65 parts of veratryl chloride, 0.11 part of NaI, 0.12 part of triethylamine, 6 parts of NaCN and 10 parts of acetone were stirred for 3.5 hours at 85° C., after which 20 parts of water were added, the mixture was stirred for 5 minutes and the phases were separated. The solvent was distilled off and the residue was then distilled under reduced pressure, 16.9 parts (95%) of VCN passing over at from 162 to 164° C. under 6 mbar. 0.9% by weight, based on distillate, of veratryl alcohol was present in the distillate.

EXAMPLE 2

The procedure described in Example 1 was followed, except that the amount of toluene was reduced to 17 parts. The reaction time was 1.5 hours. 17.2 parts (97%) of VCN were obtained. 0.8% of veratryl alcohol was present in the distillate.

EXAMPLE 3

The procedure described in Example 1 was followed, except that the amount of toluene was 44 parts, the amount of water 1.8 parts and the amount of acetone 5 parts. The reaction time was 2.5 hours. 16.8 parts (95%) of VCN were obtained. 1.2% of veratryl alcohol were present in the distillate.

EXAMPLE 4

1650 parts of a solution of crude veratryl chloride in toluene, containing 510 parts of veratryl chloride and obtained by chloromethylation of veratrol, were added, in the course of 15 minutes, to a mixture of 305 parts of toluene, 140 parts of acetone, 197 parts of NaCN, 3.1 parts of NaI, 25 parts of $H_2$ and 5.2 parts of triethylamine, the mixture having been preheated to 65° C. After the addition, stirring was continued for a further 1.5 hours at 85° C., after which 700 parts of $H_2O$ were added to the mixture, the lower aqueous phase was separated off and the organic phase was washed a second time with 200 parts of $H_2O$. The organic phase was freed from the toluene, and the residue was distilled over a column under 6 mbar and at 162°-164° C. 445 parts (92%) of VCN were obtained. 1.6% of veratryl alcohol were present in the distillate.

COMPARATIVE EXAMPLE WITHOUT THE ADDITION OF A KETONE 87 parts of toluene, 20 parts of $H_2O$, 6 parts of NaCN, 0.11 part of NaI, 0.12 part of triethylamine and 18.65 parts of veratryl chloride were stirred for 4 hours at 85° C. The aqueous phase was separated off and the organic phase was then worked up in a conventional manner to give 16.7 parts (87.5%) of VCN. 7.2% of veratryl alcohol were present in the distillate.

We claim:

1. A process for the preparation of veratryl cyanide by chloromethylating veratrol in solution in toluene and then reacting the resulting veratryl chloride with from 1 to 5 moles of an alkali metal cyanide, wherein the toluene from the chloromethylation is not removed for the reaction with cyanide, and from 3 to 25% by weight, based on veratryl chloride, of water, from 5 to 50% by weight, based on toluene, of a ketone of 3 to 6 carbon atoms and from 0.1 to 10% by weight, based on veratryl chloride, of a phase transfer catalyst are added before the reaction with cyanide.

* * * * *